(12) United States Patent
Li (10) Patent No.: US 10,295,627 B2
(45) Date of Patent: May 21, 2019

(54) PERMANENT MAGNET CONFIGURATION FOR NMR LOGGING TOOL

(71) Applicant: Halliburton Energy Services, Inc., Houston, TX (US)

(72) Inventor: Lilong Li, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 167 days.

(21) Appl. No.: 15/512,296

(22) PCT Filed: Oct. 6, 2015

(86) PCT No.: PCT/US2015/054259
§ 371 (c)(1),
(2) Date: Mar. 17, 2017

(87) PCT Pub. No.: WO2017/061992
PCT Pub. Date: Apr. 13, 2017

(65) Prior Publication Data
US 2017/0276745 A1 Sep. 28, 2017

(51) Int. Cl.
*G01V 3/00* (2006.01)
*G01R 33/383* (2006.01)
(Continued)

(52) U.S. Cl.
CPC ............ *G01R 33/383* (2013.01); *E21B 47/00* (2013.01); *G01N 24/081* (2013.01);
(Continued)

(58) Field of Classification Search
USPC ......................................................... 324/303
See application file for complete search history.

(56) References Cited

U.S. PATENT DOCUMENTS 4,714,881 A   12/1987 Givens
5,977,768 A   11/1999 Sezginer et al.
(Continued)

OTHER PUBLICATIONS

International Preliminary Report on Patentability issued in related PCT Application No. PCT/US2015/054259 dated Apr. 19, 2018 (15 pages).
(Continued)

*Primary Examiner* — Rodney E Fuller
(74) *Attorney, Agent, or Firm* — Benjamin Fite; Baker Botts L.L.P.

(57) ABSTRACT

A nuclear magnetic resonance (NMR) logging tool for use in wellbore logging operations is provided. The NMR logging tool features a three-part permanent magnet arrangement that reduces the attractive force between the NMR tool and casing, allowing the NMR tool to be lowered through wellbores of any size. Additionally, the disclosed arrangement of permanent magnets in the NMR tool may facilitate an effective pre-polarization of portions of the formation at different logging speeds. Further, the disclosed arrangement of permanent magnets in the NMR tool may provide a uniform or substantially uniform static magnetic field within the antenna window of the radio frequency (RF) antenna used to perform the measurements. The second magnet may be positioned between the first and third magnets in a longitudinal direction along the NMR tool, and a radio frequency (RF) antenna may be disposed adjacent the first magnet.

20 Claims, 3 Drawing Sheets

(51) Int. Cl.
*E21B 47/00* (2012.01)
*G01N 24/08* (2006.01)
*G01R 33/38* (2006.01)
*G01V 3/18* (2006.01)
*G01V 3/32* (2006.01)

(52) U.S. Cl.
CPC ........... *G01R 33/3808* (2013.01); *G01V 3/18* (2013.01); *G01V 3/32* (2013.01)

(56) References Cited

U.S. PATENT DOCUMENTS

| | | | | |
|---|---|---|---|---|
| 6,018,243 | A * | 1/2000 | Taicher | G01V 3/32 |
| | | | | 324/300 |
| 6,023,164 | A | 2/2000 | Prammer | |
| 6,184,681 | B1 * | 2/2001 | Heidler | G01N 24/081 |
| | | | | 324/303 |
| 6,348,792 | B1 | 2/2002 | Beard et al. | |
| 6,373,248 | B1 | 4/2002 | Poitzsch et al. | |
| 6,400,149 | B1 * | 6/2002 | Luong | G01N 24/081 |
| | | | | 324/303 |
| 6,580,273 | B2 | 6/2003 | Reiderman et al. | |
| 7,463,027 | B2 | 12/2008 | Prammer et al. | |
| 7,834,622 | B2 | 11/2010 | Reiderman et al. | |
| 2002/0125885 | A1 | 9/2002 | Reiderman et al. | |
| 2003/0132749 | A1 * | 7/2003 | Speier | G01N 24/081 |
| | | | | 324/303 |
| 2004/0066194 | A1 | 4/2004 | Slade et al. | |
| 2004/0090230 | A1 * | 5/2004 | Appel | G01N 24/081 |
| | | | | 324/307 |
| 2009/0058415 | A1 | 3/2009 | Dorovsky et al. | |
| 2013/0093422 | A1 * | 4/2013 | Morys | G01V 3/32 |
| | | | | 324/303 |
| 2015/0061665 | A1 * | 3/2015 | Reiderman | G01V 3/32 |
| | | | | 324/303 |
| 2016/0202384 | A1 * | 7/2016 | Utsuzawa | E21B 47/024 |
| | | | | 324/303 |
| 2017/0003413 | A1 * | 1/2017 | Jachmann | E21B 47/00 |
| 2017/0082773 | A1 * | 3/2017 | Xiao | G01V 3/32 |
| 2017/0242152 | A1 * | 8/2017 | Chen | E21B 49/00 |
| 2018/0267197 | A1 * | 9/2018 | Li | E21B 49/08 |

OTHER PUBLICATIONS

International Search Report and Written Opinion issued in related PCT Application No. PCT/US2015/054259 dated Jun. 29, 2016, 19 pages.

* cited by examiner

PERMANENT MAGNET CONFIGURATION FOR NMR LOGGING TOOL

CROSS-REFERENCE TO RELATED APPLICATION

The present application is a U.S. National Stage Application of International Application No. PCT/US2015/054259 filed Oct. 6, 2015, which is incorporated herein by reference in its entirety for all purposes.

TECHNICAL FIELD

The present disclosure relates generally to nuclear magnetic resonance (NMR) logging tools and, more particularly, to permanent magnet configurations for NMR logging tools used to detect wellbore properties in oil and gas wells.

BACKGROUND

Hydrocarbons, such as oil and gas, are commonly obtained from subterranean formations that may be located onshore or offshore. The development of subterranean formations and the processes involved in removing hydrocarbons from a subterranean formation typically involve a number of different steps such as, for example, drilling a wellbore at a desired well site, treating the wellbore to optimize production of hydrocarbons, and performing the necessary steps to produce and process the hydrocarbons from the subterranean formation.

Upon drilling a wellbore that intersects a subterranean hydrocarbon-bearing formation, a variety of downhole tools may be positioned in the wellbore during exploration, completion, production, and/or remedial activities. Some downhole tools are outfitted with sensors for detecting various properties of the wellbore. One available type of downhole tool is a nuclear magnetic resonance (NMR) logging tool, which can be used to measure certain properties of the geological formation through which the wellbore is drilled.

NMR tools generally include a large permanent magnet used to impose a static magnetic field downhole to preferentially align certain nuclei in the formation and thereby produce a bulk magnetization. After a change in the static field, the nuclei converge upon their equilibrium alignment with a characteristic exponential relaxation time constant known as the "spin-lattice" or "longitudinal" relaxation time T1. Another relaxation time constant that can be measured is the "spin-spin" or "transverse" relaxation time T2. The tool applies a radio frequency electromagnetic pulse whose magnetic component is perpendicular to the static field produced by the permanent magnet. This pulse tips the nuclei's magnetic orientation into the transverse (perpendicular) plane and, once the pulse ends, causes them to precess ("spin") in the transverse plane as they realign themselves with the static field. This T2 relaxation time constant represents how quickly the transverse plane magnetization disperses through de-phasing and magnitude loss. The precessing nuclei generate a detectable radio frequency signal that can be used to measure statistical distributions of T1 and T2, from which other formation properties such as porosity, permeability, and hydrocarbon saturation can be determined.

When such NMR logging tools are deployed into a wellbore, they generally must first pass through a section of casing. This casing is often made of magnetic steel. During this process, an attractive force may be generated between the steel casing and the large permanent magnet in the NMR tool. Such attractive force between the casing and the NMR tool can keep the NMR tool from dropping down the wellbore, especially in deviated wells. NMR tools used in large wellbores are equipped with a pad to reduce the magnetic attractive force between the tool and the casing. Unfortunately, this type of pad can add undesirable bulk to the NMR tool, making the tool unsuitable for use in smaller wellbores.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

Illustrative embodiments of the present disclosure are described in detail herein. In the interest of clarity, not all features of an actual implementation are described in this specification. It will, of course, be appreciated that in the development of any such actual embodiment, numerous implementation-specific decisions must be made to achieve developers' specific goals, such as compliance with system-related and business-related constraints, which will vary from one implementation to another. Moreover, it will be appreciated that such a development effort might be complex and time consuming, but would nevertheless be a routine undertaking for those of ordinary skill in the art having the benefit of the present disclosure. Furthermore, in no way should the following examples be read to limit, or define, the scope of the disclosure.

Certain embodiments according to the present disclosure may be directed to systems and methods for reducing attractive force between a nuclear magnetic resonance (NMR) logging tool and a wellbore casing, while maintaining a desired static magnetic field in an antenna window of the NMR logging tool and generating a desired pre-polarization for the spins in the formation. In certain NMR logging tools, it is desirable to provide a static magnetic field within an antenna window of approximately 14 to 16 inches long, requiring a relatively large permanent magnet positioned relative to the antenna window. That is, the magnet would have to extend at least approximately three feet in each logging direction to provide a desired uniform magnetic field within the antenna window. Even at this length, such a permanent magnet may still not provide enough magnetization to pre-polarize the nuclei in the formation as the NMR logging tool is moved through the wellbore at certain speeds. Pre-polarization may refer to the time it takes for the magnetic field established by the permanent magnet to align the nuclei in the formation for the tool measurements. To provide the desired pre-polarization, the permanent magnet would have to be further elongated, or an additional magnet would have to be added to one or both sides of the first permanent magnet.

Unfortunately, such a large magnet (or pair of magnets) could generate a relatively high attractive force between the NMR tool and a casing of the wellbore. When the NMR logging tool is deployed into a wellbore, it generally passes through a section of casing made of magnetic steel. During this process, an attractive force may be generated between the steel casing and the large permanent magnet(s) in the NMR tool, particularly in side-looking NMR tools. The attractive force may be more pronounced for NMR tools being lowered through relatively small wellbores (e.g., with casing of approximately 7 inches in diameter) and/or deviated wellbores. Such attractive forces between the casing and the NMR tool can prevent the NMR tool from dropping down the wellbore to perform the desired logging.

To overcome these drawbacks, the present embodiments are directed to a NMR logging tool with a specific three-part permanent magnet arrangement that reduces the attractive force between the NMR tool and casing, thereby allowing the NMR tool to be lowered through wellbores of any desired size. In addition, the disclosed arrangement of permanent magnets in the NMR tool may facilitate an effective pre-polarization of portions of the formation at different logging speeds. Pre-polarization refers to the time needed for the nuclei (i.e., protons) in the formation to align in a certain direction needed for the NMR measurements. Further, the disclosed arrangement of permanent magnets in the NMR tool may provide a uniform or substantially uniform static magnetic field within the antenna window of the radio frequency (RF) antenna used to perform the measurements.

To that end, the disclosed permanent magnet arrangement may include at least three separate permanent magnets positioned within the NMR logging tool in an arrangement that provides the effects described herein. Specifically, the NMR logging tool may include a first permanent magnet disposed at a first longitudinal position within the NMR tool, a second permanent magnet disposed at a second longitudinal position within the NMR tool, and a third permanent magnet disposed at a third longitudinal position within the NMR tool. The second permanent magnet may be positioned between the first and third permanent magnets in a longitudinal direction along the NMR tool, and the antenna may be disposed adjacent the first permanent magnet. The at least three permanent magnets may be arranged specifically to prevent an undesirable attractive force toward the casing while maintaining proper logging functions of the NMR tool. This may enable the NMR tool to operate in wellbores of all sizes and deviations without becoming stuck in a casing, as well as to provide more accurate measurements.

Figure 1:
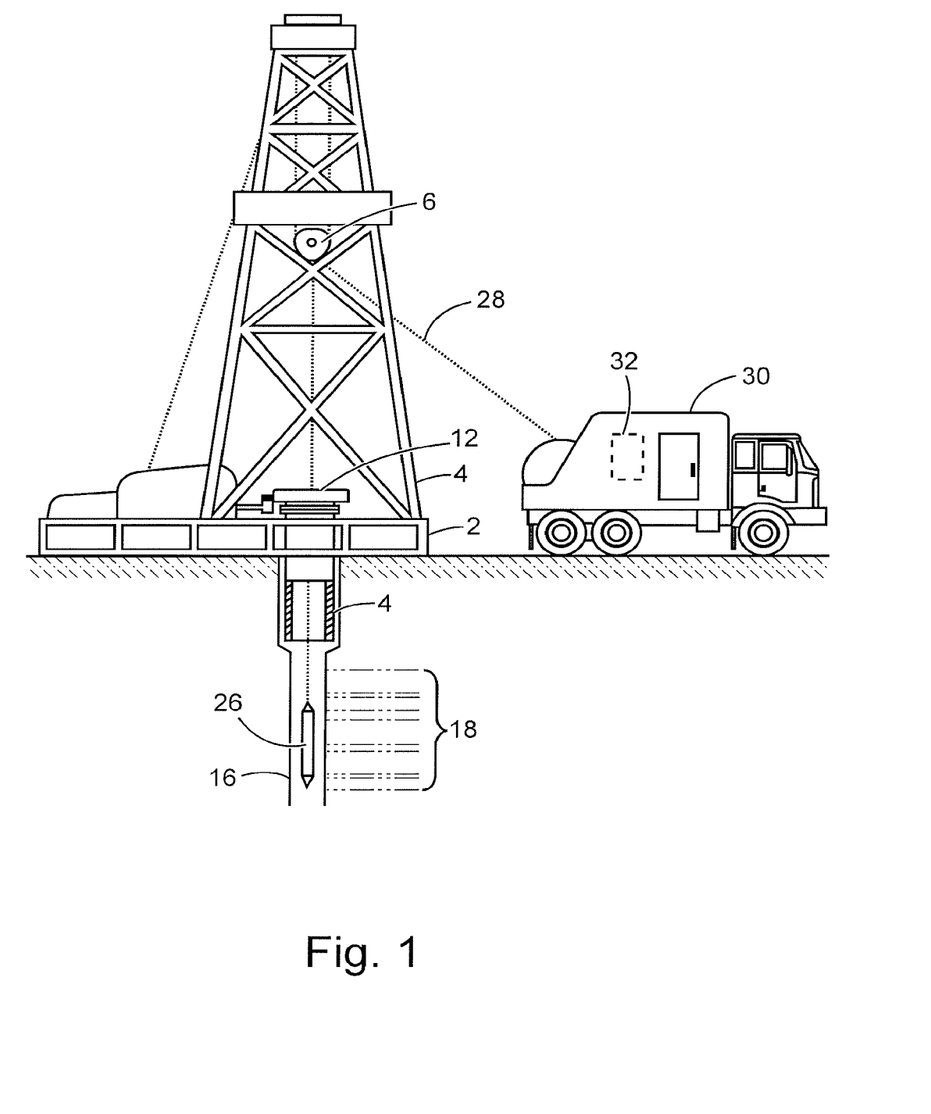
FIG. 1 is a partial cutaway schematic view of a well environment for wireline logging with a nuclear magnetic resonance (NMR) logging tool, in accordance with an embodiment of the present disclosure.

Turning now to the drawings, FIG. 1 illustrates oil well equipment being used in an illustrative drilling environment. A drilling platform 2 supports a derrick 4 having a traveling block 6 for raising and lowering a drill string (not shown). The drill string creates a wellbore 16 that passes through various formations 18. At various times during the drilling process, the drill string may be removed from the wellbore 16.

Once the drill string has been removed, logging operations can be conducted using a wireline logging tool 26. The wireline logging tool 26 may include a sensing instrument sonde suspended by a cable 28 having conductors for transporting power to the tool and telemetry from the tool to the surface. As discussed in detail below, the wireline logging tool 26 may include a NMR logging instrument that collects measurements relating to spin relaxation time distributions as a function of depth or position in the wellbore 16.

A logging facility 30 may collect measurements from the logging tool 26. Specifically, signals collected from the logging tool 26 may be communicated to the logging facility 30 via the cable 28. The logging facility 30 may include a computer system 32 for processing and storing the measurements gathered by the logging tool 26. More specifically, the computer system 32 may include a processing component for determining one or more properties of the formation based on signals detected by an RF antenna of the logging tool 26.

In other embodiments, the logging tool 26 may be a tubing-conveyed logging tool. Tubing-conveyed logging is similar to wireline logging, except that a tubing string is used to move the formation tester/NMR logging instrument 26 through the wellbore 16.

The formation testing/NMR logging tool 26 may include an arrangement of three or more permanent magnets to provide an azimuthally-symmetric static magnetic field. The NMR logging tool 26 may also include one or more RF antennas designed to detect signals from excited nuclei of the formation 18 within an antenna window of examination. More specifically, the RF antennas may provide a radio frequency magnetic field perpendicular to the static field and detect the electromagnetic signature of the nuclei's precession as they realign themselves with the static field. Permeable materials may be employed to enhance sensitivity of the antennas as well as for favorably shaping field lines. Such permeable materials may be positioned directly underneath the antennas.

As mentioned above, the NMR logging tool 26 may feature a specific arrangement of permanent magnets that are designed to generate the substantially static magnetic field within the antenna window of the tool's one or more RF antennas, while preventing undesired attractive forces between the NMR tool 26 and a casing 34 and providing a desired pre-polarization of nuclei within the formation 18. One embodiment of a three-part permanent magnet arrangement 50 is illustrated in FIGS. 2, 3, and 4A-4C.

Figure 2:
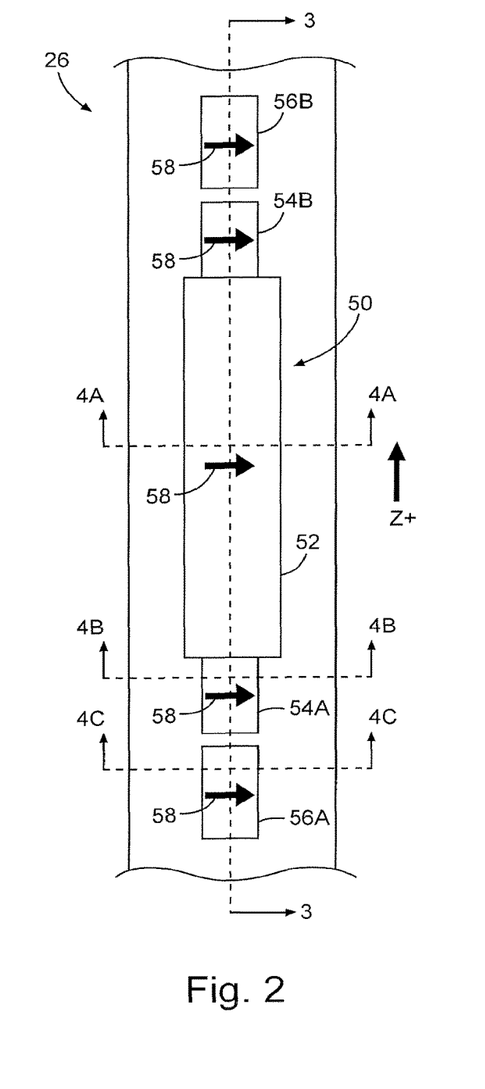
FIG. 2 is a side view of a three-part permanent magnet arrangement for use in a NMR logging tool, in accordance with an embodiment of the present disclosure.
Figure 3:
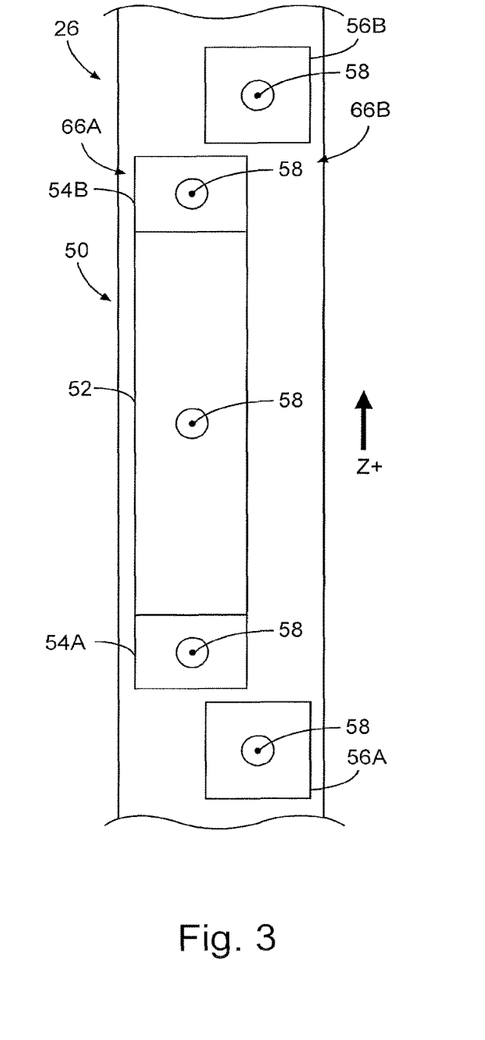
FIG. 3 is another side view of the three-part permanent magnet arrangement of FIG. 2, in accordance with an embodiment of the present disclosure.
Figure 4A:
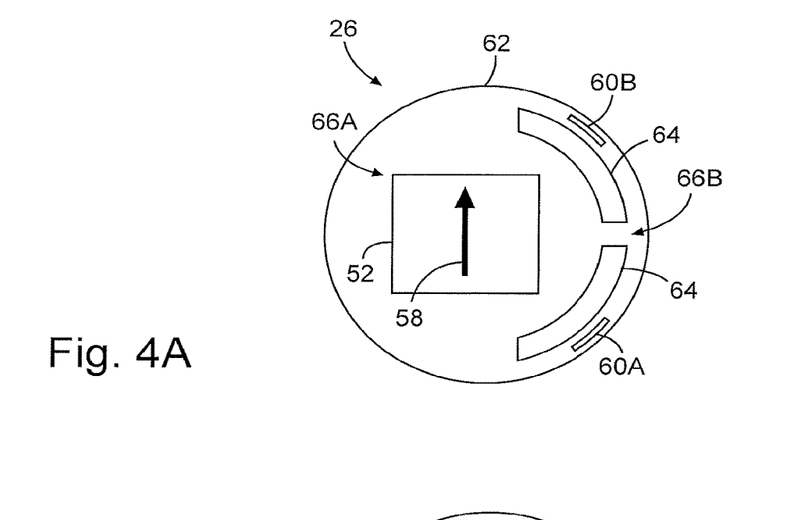
FIGS. 4A-4C are cross sectional view of each of the three permanent magnets used in the permanent magnet arrangement of FIGS. 2 and 3, in accordance with an embodiment of the present disclosure.
Figure 4B:
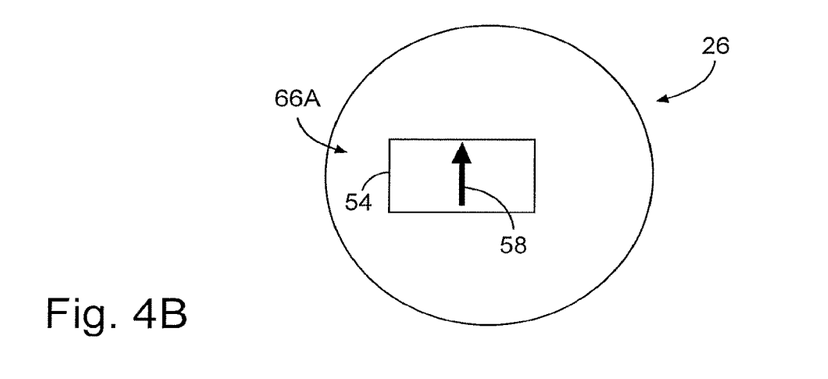
Figure 4C:
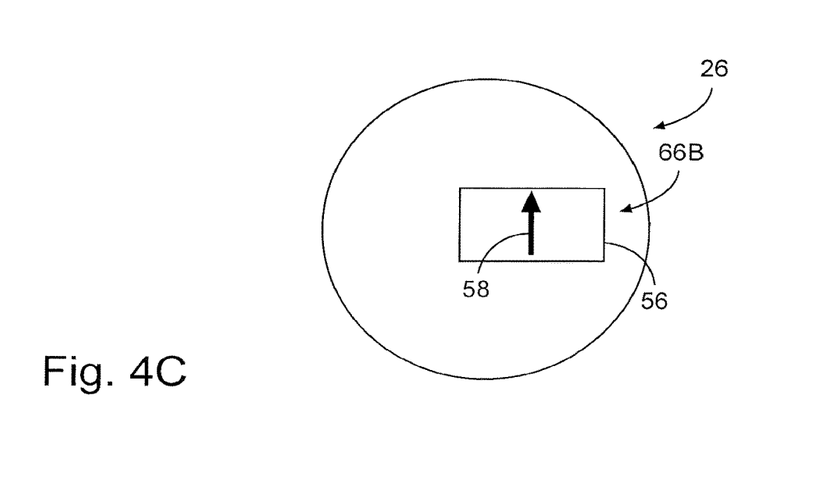

FIG. 2 is a side view of the permanent magnet arrangement 50 having at least three sections 52, 54, and 56. FIG. 3 is another side view of the permanent magnet arrangement 50, taken from a plane perpendicular to the viewing plane of FIG. 2. FIGS. 4A-4C illustrate cross-sectional views of the NMR logging tool 26 at each of the three sections 52, 54, and 56. Although only one configuration of the permanent magnets 52, 54, and 56 is illustrated in these figures, it should be noted that several other configurations and relative dimensions of the at least three permanent magnets 52, 54, and 56 may be used in other embodiments to provide similar effects.

In the illustrated embodiment, arrows 58 are shown to represent the direction of magnetization of each of the at least three permanent magnets 52, 54, and 56. As illustrated, the magnets 52, 54, and 56 are aligned so that the direction of magnetization is the same for all of the magnets 52, 54, and 56.

As shown in FIGS. 2 and 3, the magnet arrangement 50 may include five separate permanent magnets 52, 54A, 54B, 56A, and 56B. That is, there are two sets of magnets for each of the second section 54 and the third section 56. This arrangement 50 may be desirable in embodiments of the NMR tool 26 where the NMR tool 26 is designed to perform logging functions while being moved through the wellbore in both directions. More specifically, the five-magnet arrangement may enable the NMR tool 26 to perform NMR measurements while the tool 26 is moving downward (e.g., in the negative Z-axis direction) through the wellbore and while the tool 26 is moving upward (e.g., in the positive Z-axis direction) through the wellbore. The second and third magnet sections 54A and 56A in one direction may help the NMR tool 26 perform accurate measurements while the NMR tool 26 is moving downward. Similarly, the second and third magnet sections 54B and 56B in the opposite direction may help the NMR tool 26 perform accurate measurements while the NMR tool 26 is moving upward.

It should be noted, however, that other embodiments of the magnet arrangement 50 may only include three permanent magnets 52, 54, and 56 (one of each section) arranged longitudinally throughout the NMR logging tool 26. In such embodiments, the NMR tool 26 may be limited to detecting measurements of the formation while traveling through the wellbore in a single direction. For example, if the first magnet 52 is disposed above the second magnet 54 and the second magnet 54 is disposed above the third magnet 56, the magnet arrangement 50 may be suitable for detecting formation properties only while the NMR tool 26 is moved downward through the wellbore. If the first magnet 52 is disposed beneath the second magnet 54 and the second magnet 54 is disposed beneath the third magnet 56, the magnet arrangement 50 may be suitable for detecting formation properties only while the NMR tool 26 is moved upward through the wellbore.

In some embodiments, all the magnets 52, 54, and 56 provided in the magnet arrangement 50 may be made from the same magnetic material. For example, each of the magnets 52, 54, and 56 may be constructed from samarium cobalt. However, in other embodiments one or more of the at least three magnets 52, 54, and 56 may be constructed from different types of magnetic material. In the illustrated embodiment, each of the magnets 52, 54, and 56 may have a prismatic volume with a rectangular cross section. However, it should be noted that the magnets 52, 54, and 56 may be present in the NMR tool 26 in any desired shape for providing the desired uniform static magnetic field.

As illustrated in FIG. 4A, the first magnet section (e.g., having the first permanent magnet 52) of the NMR tool 26 may include a RF antenna 60. That is, the RF antenna 60 may also be disposed at approximately the first longitudinal position within the NMR tool 26. The RF antenna 60 may be used to detect signals from excited nuclei of the formation within an antenna window of examination. The term "antenna window" refers to the sensing range of the RF antenna 60 in a desired direction. In some embodiments, the first permanent magnet 52 may extend beyond the antenna window in a longitudinal direction (i.e., direction of Z-axis). As shown in FIG. 4A, the RF antenna 60 may be disposed within a housing 62 of the NMR tool 26. In some embodiments, the RF antenna 60 may extend longitudinally through the NMR tool 26 on two sides 60A and 60B as well as radially around the NMR tool 26 to connect these two sides 60A and 60B. However, other antenna configurations may be utilized in other embodiments of the disclosed NMR tool 26.

In addition to the antenna 60, the first section of the NMR tool 26 may also include a soft magnetic material 64 to help maximize the efficiency of the RF antenna 60. The soft magnet material 64 may be disposed between the first permanent magnet 52 and the RF antenna 60 to keep the first magnet 52 from affecting the antenna operation. As illustrated in FIG. 4A, the permanent magnet 52 may be positioned slightly to one side 66A of the NMR tool 26, while the soft magnetic material 64 and the antenna 60 are positioned slightly to an opposite side 66B of the NMR tool 26. These two sides 66A and 66B may extend in opposing lateral directions from a central longitudinal axis of the NMR tool 26.

Such soft magnetic material 64 has a relatively high permeability, which can cause the soft magnetic material 64 to effectively "short" the magnetic field produced by the first permanent magnet 52. This may lead to a reduced-strength magnetic field provided by the first magnet 52 to the area of interest (i.e., antenna window) of the formation. In embodiments of the NMR tool 26 where soft magnetic material is not used, the first permanent magnet 52 may be sized smaller than in embodiments where soft magnetic material 64 is used to achieve the same magnetic field strength.

In the disclosed embodiments, the magnet arrangement 50 may include the second permanent magnet 54 to help provide the desired magnetic field strength within the antenna window. As shown in FIG. 4B, the second magnet section (e.g., having the second permanent magnet 54) may not include the soft magnetic material and, as a result, may help to produce a larger magnetic field within the antenna window than would be available using just the first magnet 52.

As shown in FIGS. 2, 4A, and 4B, the second magnet 54 may have a relatively smaller cross section (in a plane perpendicular to the longitudinal Z-axis of the NMR tool 26) than the first magnet 52. The second magnet 54 may therefore have a smaller 2D azimuthal magnetic dipole moment than the first magnet 52, while maintaining approximately the same magnetic field strength at the same depth of investigation. This is because the second magnet 54 does not feature any soft magnetic material that would otherwise short the magnet 54. Since the second magnet 54 is smaller (i.e., features a smaller 2D azimuthal dipole moment), this may help reduce the attractive force that might otherwise be applied to the casing of the wellbore if the NMR tool had a single elongated magnet.

The second magnet 54 may have a cross section that is specifically designed to make the magnetic field within the antenna window of the NMR tool 26 as uniform as possible. That is, the size of the second magnet 54 may be fine-tuned to provide the desired substantially uniform static magnetic field within the antenna window. The substantially uniform magnetic field provided by the NMR tool 26 may help to minimize measurement losses due to movement of the tool 26 during a logging operation. Such flexibility to fine tune the magnet size and therefore reach a desired magnetic field homogeneity requirement may not be available when using only a single elongated magnet.

As mentioned above, the disclosed magnet arrangement 50 may also include the third magnet section 56 (i.e., third permanent magnet). As illustrated in FIGS. 2 and 3, the permanent magnets 52, 54, and 56 are arranged such that the second magnet 54 (A or B) is disposed between the first magnet 52 and the corresponding third magnet 56 (A or B, respectively). Thus, the third magnet section 56 may follow the second magnet section 54 in a direction away from the first magnet section 52. As shown, the third magnet section 56 may extend further in a longitudinal direction (Z-axis) than the second magnet section 54. However, the second and third magnets 54 and 56 may have approximately the same cross sectional area in a plane perpendicular to the longitudinal Z-axis, which is less than the cross sectional area of the first magnet 52.

The third magnet 56 may have a higher field strength at the same depth of investigation, compared to the second magnet 54, to provide sufficient pre-polarization of the formation during logging operations as the NMR tool 26 moves through the wellbore. That is, the third magnet section 56 may expose a portion of the formation to a magnetic field prior to that portion of the formation entering the antenna window. By the time the NMR tool 26 has moved through the wellbore such that the portion of the formation is in the antenna window for measurements via the RF antenna 60, the portion may be fully polarized and aligned with the substantially uniform static magnetic field provided by the first and second magnets 52 and 54.

In order to maintain the desired magnetic field uniformity within the antenna window, a cross sectional center of the first two magnets 52 and 54 (in a plane perpendicular to the Z-axis) may be positioned at approximately the same point. That is, the first and second magnets 52 and 54 in the NMR tool 26 may be disposed directly over one another in the longitudinal direction of the Z-axis. In some embodiments, these magnets 52 and 54 may be in direct contact with each other. In other embodiments, the magnets 52 and 54 may be spaced in the longitudinal direction from each other. Either way, it may be desirable for their cross sectional centers (in a plane perpendicular to the longitudinal Z-axis of the NMR tool 26) to be approximately the same within the NMR tool 26. This placement may allow the NMR tool 26 to produce a substantially uniform static magnetic field in the antenna window.

The third magnet 56, however, is far enough positioned from the antenna window that it may be centered at any point in the NMR tool 26 without affecting the uniformity of the magnetic field within the antenna window. As shown in FIGS. 3 and 4C, for example, the third magnet 56 may be disposed on an opposite side 66B of the NMR tool 26 from the first and second magnets 52 and 54 (positioned on side 66A). In FIG. 2, all three magnet sections 52, 54, and 56 appear to be centered along a longitudinal center line through the NMR tool 26. However, when viewed from an orthogonal plane (FIGS. 3 and 4), the third magnet 56 may be offset from the first and second magnets 52 and 54.

This placement of the third magnet 56 may help to counteract the effects of an attractive force between the first and second magnets 52 and 54 and a wellbore casing. In a relatively small wellbore, for example, the NMR tool 26 may experience an attractive force toward the casing in one direction due to the first and second magnets 52 and 54, as well as an opposing attractive force toward the casing in an opposite direction due to the third magnet 56. These attractive forces may cancel each other out to a certain extent, thereby reducing the overall force on the NMR tool 26 and enabling the tool to pass through the cased section of the wellbore.

In the illustrated embodiment of FIGS. 2 and 3, the third magnet 56 may be spaced in a longitudinal direction (i.e., Z-axis) from the second magnet 54. However, in other embodiments, the third magnet 56 may be disposed in direct contact with the second magnet 54.

As discussed above, the magnet arrangement 50 provided in FIGS. 2 and 3 is symmetric with respect to the azimuthal plane of measurement in the middle of the first magnet section 52. This allows the illustrated NMR tool 26 to perform logging operations while moving upward through the wellbore as well as downward through the wellbore. However, it should be noted that embodiments of the magnet arrangement 50 may include at least three magnet sections in either logging direction (up or down), or three magnet sections arranged in both logging directions.

The magnet arrangement 50 provided in FIGS. 2-4 may be designed for use within a side-looking NMR tool 26. A side-looking NMR tool 26 may provide NMR measurements along just one side of the wellbore. These side-looking NMR measurements generally have higher sensitivities than those available using a centralized NMR tool. Although illustrated herein as used in a side-looking tool, in other embodiments the three-magnet arrangement 50 may be applied to a centralized NMR tool 26. In such embodiments, the magnet sections 52, 54, and 56 may all be aligned in a longitudinal direction. That is, the center points of all three magnet sections 52, 54, and 56 may be aligned with a central longitudinal axis of the NMR tool 26.

Embodiments disclosed herein include:

A. A nuclear magnetic resonance (NMR) logging tool for use in a wellbore. The NMR logging tool includes a first permanent magnet disposed at a first longitudinal position within the NMR logging tool, a radio frequency (RF) antenna disposed proximate the first permanent magnet at the first longitudinal position for detecting signals from excited nuclei within an antenna window of examination, a second permanent magnet disposed at a second longitudinal position within the NMR logging tool, and a third permanent magnet disposed at a third longitudinal position within the NMR logging tool. The second permanent magnet is located between the first permanent magnet and the third permanent magnet in a direction of a longitudinal axis of the NMR logging tool.

B. A method including moving a nuclear magnetic resonance (NMR) logging tool through a wellbore extending into a formation and establishing a static magnetic field within an antenna window of a radio frequency (RF) antenna of the NMR logging tool, via a first permanent magnet, a second permanent magnet, and a third permanent magnet disposed within the NMR logging tool. The first, second, and third permanent magnets are disposed at different longitudinal positions along the NMR logging tool, the second permanent magnet is located between the first permanent magnet and the third permanent magnet, and the RF antenna is disposed proximate and at approximately the same longitudinal position as the first permanent magnet. The method also includes establishing a region of interest via the static magnetic field in the antenna window, exciting nuclei of the formation in the region of interest via RF pulses produced by the RF antenna, and detecting one or more signals from excited nuclei within the antenna window via the RE antenna.

Each of the embodiments A and B may have one or more of the following additional elements in combination: Element 1: wherein the first and second permanent magnets are positioned on a first lateral side of the NMR logging tool, and wherein the third permanent magnet is positioned on a second lateral side of the NMR logging tool opposite the first lateral side, and wherein the NMR logging tool is a side-looking tool. Element 2: wherein the first, second, and third permanent magnets are each centered on the longitudinal axis of the NMR logging tool, and wherein the NMR logging tool is a centralized tool. Element 3: wherein the NMR logging tool is sized to fit through a wellbore with casing having a diameter of approximately seven inches. Element 4: wherein a dipole moment of the first permanent magnet is larger than a dipole moment of the second permanent magnet. Element 5: wherein the first and second permanent magnets are disposed immediately adjacent each other, and wherein the third permanent magnet is spaced from the second permanent magnet in the direction of the longitudinal axis. Element 6: wherein a cross section of the first permanent magnet taken in a plane perpendicular to the longitudinal axis is greater than a cross section of the second permanent magnet taken in a plane perpendicular to the longitudinal axis. Element 7: wherein the third permanent magnet extends further in a longitudinal direction of the NMR logging tool than the second permanent magnet to produce a higher magnetic field strength. Element 8: further including soft magnetic material disposed proximate the first permanent magnet at the first longitudinal position for increasing an efficiency of the RF antenna. Element 9: wherein the second permanent magnet is sized to produce a substantially uniform static magnetic field within the antenna window of examination. Element 10: wherein the third permanent magnet is disposed at the third longitudinal position within the NMR logging tool to provide pre-polarization of a portion of a formation before the portion of the formation reaches the antenna window of examination during logging operations. Element 11: further including a fourth permanent magnet disposed at a fourth longitudinal position within the NMR logging tool and a fifth permanent magnet disposed at a fifth longitudinal position within the NMR logging tool, wherein the fourth permanent magnet is disposed on an opposite side of the first permanent magnet from the second permanent magnet and is located between the first permanent magnet and the fifth permanent magnet.

Element 12: further including determining via a processing component one or more properties of the formation based on the signals detected by the RF antenna. Element 13: further including establishing a substantially uniform static magnetic field within the antenna window via the first and second permanent magnets. Element 14: further including providing pre-polarization of nuclei in the formation as the NMR logging tool moves through the wellbore via the second and third permanent magnets. Element 15: further including establishing an attractive force between a first side of the NMR logging tool and a casing in the wellbore via the first and second permanent magnets, and establishing an opposing attractive force between a second side of the NMR logging tool opposite the first side and the casing via the third permanent magnet. Element 16: further including moving the NMR logging tool through a casing with a diameter of less than or equal to seven inches. Element 17: further including logging NMR measurement data in a first direction through the wellbore and in a second direction through the wellbore opposite the first direction, via the NMR logging tool. Element 18: further including establishing the static magnetic field within the antenna window, via the first permanent magnet, the second permanent magnet, and the third permanent magnet of the NMR logging tool as the NMR logging tool is moving in the first direction through the wellbore, and establishing a static magnetic field within the antenna window, via the first permanent magnet, a fourth permanent magnet, and a fifth permanent magnet of the NMR logging tool as the NMR logging tool is moving in the second direction through the wellbore, wherein the first, fourth, and fifth permanent magnets are disposed at different longitudinal positions along the NMR logging tool, and wherein the fourth permanent magnet is located between the first permanent magnet and the fifth permanent magnet.

Although the present disclosure and its advantages have been described in detail, it should be understood that various changes, substitutions and alterations can be made herein without departing from the spirit and scope of the disclosure as defined by the claims.

What is claimed is:
1. A nuclear magnetic resonance (NMR) logging tool for use in a wellbore, comprising:
 a first permanent magnet disposed at a first longitudinal position within the NMR logging tool;
 a radio frequency (RF) antenna disposed proximate the first permanent magnet at the first longitudinal position for detecting signals from excited nuclei within an antenna window of examination;
 a second permanent magnet disposed at a second longitudinal position within the NMR logging tool; and
 a third permanent magnet disposed at a third longitudinal position within the NMR logging tool;
 wherein the second permanent magnet is located between the first permanent magnet and the third permanent magnet in a direction of a longitudinal axis of the NMR logging tool;
 wherein the first and second permanent magnets are positioned on a first lateral side of the NMR logging tool, and wherein the third permanent magnet is positioned on a second lateral side of the NMR logging tool opposite the first lateral side, and wherein the NMR logging tool is a side-looking tool.

2. The NMR logging tool of claim 1, wherein the NMR logging tool is sized to fit through a wellbore with casing having a diameter of approximately seven inches.

3. The NMR logging tool of claim 1, wherein a dipole moment of the first permanent magnet is larger than a dipole moment of the second permanent magnet.

4. The NMR logging tool of claim 1, wherein a cross section of the first permanent magnet taken in a plane perpendicular to the longitudinal axis is greater than a cross section of the second permanent magnet taken in a plane perpendicular to the longitudinal axis.

5. The NMR logging tool of claim 1, wherein the third permanent magnet extends further in a longitudinal direction of the NMR logging tool than the second permanent magnet to produce a higher magnetic field strength.

6. The NMR logging tool of claim 1, further comprising soft magnetic material disposed proximate the first permanent magnet at the first longitudinal position for increasing an efficiency of the RF antenna.

7. The NMR logging tool of claim 1, wherein the second permanent magnet is sized to produce a substantially uniform static magnetic field within the antenna window of examination.

8. The NMR logging tool of claim 1, wherein the third permanent magnet is disposed at the third longitudinal position within the NMR logging tool to provide pre-polarization of a portion of a formation before the portion of the formation reaches the antenna window of examination during logging operations.

9. The NMR logging tool of claim 1, further comprising a fourth permanent magnet disposed at a fourth longitudinal position within the NMR logging tool and a fifth permanent magnet disposed at a fifth longitudinal position within the NMR logging tool, wherein the fourth permanent magnet is disposed on an opposite side of the first permanent magnet from the second permanent magnet and is located between the first permanent magnet and the fifth permanent magnet.

10. A method, comprising:
 moving a nuclear magnetic resonance (NMR) logging tool through a wellbore extending into a formation;
 establishing a static magnetic field within an antenna window of a radio frequency (RF) antenna of the NMR logging tool, via a first permanent magnet, a second permanent magnet, and a third permanent magnet disposed within the NMR logging tool, wherein the first, second, and third permanent magnets are disposed at different longitudinal positions along the NMR logging tool, wherein the second permanent magnet is located between the first permanent magnet and the third permanent magnet, and wherein the RF antenna is disposed proximate and at approximately the same longitudinal position as the first permanent magnet;

establishing a region of interest via the static magnetic field in the antenna window;

exciting nuclei of the formation in the region of interest via RF pulses produced by the RF antenna;

detecting one or more signals from excited nuclei within the antenna window via the RF antenna;

establishing an attractive force between a first side of the NMR logging tool and a casing in the wellbore via the first and second permanent magnets; and establishing an opposing attractive force between a second side of the NMR logging tool opposite the first side and the casing via the third permanent magnet.

11. The method of claim 10, further comprising determining via a processing component one or more properties of the formation based on the signals detected by the RF antenna.

12. The method of claim 10, further comprising establishing a substantially uniform static magnetic field within the antenna window via the first and second permanent magnets.

13. The method of claim 10, further comprising providing pre-polarization of nuclei in the formation as the NMR logging tool moves through the wellbore via the second and third permanent magnets.

14. The method of claim 10, further comprising moving the NMR logging tool through the casing, wherein the casing has a diameter of less than or equal to seven inches.

15. The method of claim 10, further comprising logging NMR measurement data in a first direction through the wellbore and in a second direction through the wellbore opposite the first direction, via the NMR logging tool.

16. The method of claim 15, further comprising:
establishing the static magnetic field within the antenna window, via the first permanent magnet, the second permanent magnet, and the third permanent magnet of the NMR logging tool as the NMR logging tool is moving in the first direction through the wellbore; and
establishing a static magnetic field within the antenna window, via the first permanent magnet, a fourth permanent magnet, and a fifth permanent magnet of the NMR logging tool as the NMR logging tool is moving in the second direction through the wellbore, wherein the first, fourth, and fifth permanent magnets are disposed at different longitudinal positions along the NMR logging tool, and wherein the fourth permanent magnet is located between the first permanent magnet and the fifth permanent magnet.

17. A nuclear magnetic resonance (NMR) logging tool for use in a wellbore, comprising:
a first permanent magnet disposed at a first longitudinal position within the NMR logging tool;
a radio frequency (RF) antenna disposed proximate the first permanent magnet at the first longitudinal position for detecting signals from excited nuclei within an antenna window of examination;
a second permanent magnet disposed at a second longitudinal position within the NMR logging tool; and
a third permanent magnet disposed at a third longitudinal position within the NMR logging tool;
wherein the second permanent magnet is located between the first permanent magnet and the third permanent magnet in a direction of a longitudinal axis of the NMR logging tool;
wherein the first and second permanent magnets are disposed immediately adjacent each other, and wherein the third permanent magnet is spaced from the second permanent magnet in the direction of the longitudinal axis.

18. The NMR logging tool of claim 17, wherein the first and second permanent magnets are positioned on a first lateral side of the NMR logging tool, and wherein the third permanent magnet is positioned on a second lateral side of the NMR logging tool opposite the first lateral side, and wherein the NMR logging tool is a side-looking tool.

19. The NMR logging tool of claim 17, wherein the first, second, and third permanent magnets are each centered on the longitudinal axis of the NMR logging tool, and wherein the NMR logging tool is a centralized tool.

20. The NMR logging tool of claim 17, further comprising soft magnetic material disposed proximate the first permanent magnet at the first longitudinal position for increasing an efficiency of the RF antenna.

* * * * *